United States Patent
Kim et al.

(10) Patent No.: US 7,290,489 B2
(45) Date of Patent: Nov. 6, 2007

(54) SUBSTRATE INSPECTING APPARATUS AND CONTROL METHOD THEREOF

(75) Inventors: Dae-jung Kim, Seoul (KR); Sang-jin Choi, Yongin-si (KR); Jong-han Oh, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 166 days.

(21) Appl. No.: 11/127,198

(22) Filed: May 12, 2005

(65) Prior Publication Data
US 2006/0044378 A1   Mar. 2, 2006

(51) Int. Cl.
*G06K 9/00* (2006.01)

(52) U.S. Cl. .................. 101/484; 101/483; 382/112; 347/104

(58) Field of Classification Search ............... None
See application file for complete search history.

(56) References Cited

U.S. PATENT DOCUMENTS 5,047,870 A * 9/1991 Filo ................... 358/472
5,757,388 A * 5/1998 Stephenson ............ 347/2
5,980,010 A * 11/1999 Stephenson ............ 347/2
6,373,964 B1  4/2002 Geissler et al.
6,456,733 B1  9/2002 Miyauchi et al.

FOREIGN PATENT DOCUMENTS

| JP | 11-344449 | | 12/1999 |
| JP | 2001078029 | A * | 3/2001 |
| JP | 2005205853 | A * | 8/2005 |
| KR | 1999-32185 | | 7/1999 |

* cited by examiner

*Primary Examiner*—Jill E. Culler
(74) *Attorney, Agent, or Firm*—Stanzione & Kim, LLP

(57) ABSTRACT

A substrate inspecting apparatus to inspect a substrate printed on by a print head to determine whether a printing operation is being accurately performed includes a camera unit to photograph the substrate before the substrate is printed on and to photograph the substrate after the substrate is printed on, and a control part to compare a first image of the substrate before the substrate is printed on with a second image of the substrate after the substrate is printed on through the camera unit and to determine whether the printing operation is being accurately performed on the substrate. Thus, the substrate inspecting apparatus is capable of precisely inspecting the substrate during the printing operation and reducing processing time.

42 Claims, 4 Drawing Sheets

SUBSTRATE INSPECTING APPARATUS AND CONTROL METHOD THEREOF

CROSS-REFERENCE TO RELATED APPLICATIONS

This application claims the benefit of Korean Patent Application No. 2004-67478, filed on Aug. 26, 2004, in the Korean Intellectual Property Office, the disclosure of which is incorporated herein in its entirety by reference.

BACKGROUND OF THE INVENTION

1. Field of the Invention

The present general inventive concept relates to a substrate inspecting apparatus, and more particularly to, a substrate inspecting apparatus to inspect a substrate to determine whether a printing operation is being accurately performed thereon, and a control method thereof.

2. Description of the Related Art

Flat display apparatuses, such as thin film transistor-liquid crystal displays (TFT-LCD) and organic electro luminescence displays (ELD), are generally provided with display panels on which images are formed.

A process of manufacturing a display panel comprises a printing process to form a color filter on a display panel substrate. Inkjet devices have been used in the printing process.

Using an inkjet device, ink to form the color filter is ejected from a plurality of orifices on a print head and then cured on a plurality of pixels formed on the display panel substrate.

A substrate inspecting apparatus may be used in the printing process to inspect colors and positions of ink printed on a transparent substrate.

A conventional substrate inspecting apparatus obtains images by positioning a printed transparent substrate on a white background inspection base and photographing it with a camera after a printing operation has been performed on the transparent substrate by the print head. Using images of the printed transparent substrate photographed in this manner, colors and positions of ink printed on the transparent substrate are inspected to determine whether the printing operation was performed accurately on the transparent substrate.

However, since this conventional substrate inspecting apparatus typically uses the white background inspection base to inspect the printed transparent substrate, the white background inspection base may be stained with ink during the printing operation. When the white background inspection base is stained with ink, exact images of the printed transparent substrate cannot be obtained in an inspection operation. As a result, precise inspection is not possible.

When using the conventional substrate inspecting apparatus, the printing operation and the inspection operation are performed separately, since the inspection operation typically must be performed after the printing operation has been completed on the transparent substrate. If the printing operation and the inspection operation are performed simultaneously, no separate inspection time is needed, thereby effectively reducing processing time.

SUMMARY OF THE INVENTION

The present general inventive concept provides a substrate inspecting apparatus capable of precisely inspecting a substrate to determine whether a printing operation is accurately performed and reducing processing time and a control method thereof.

Additional aspects and/or advantages of the present general inventive concept will be set forth in part in the description which follows and, in part, will be obvious from the description, or may be learned by practice of the general inventive concept.

The foregoing and/or other aspects of the present general inventive concept are achieved by providing a substrate inspecting apparatus to inspect a substrate printed on by a print head to determine whether a printing operation is accurately performed, comprising a camera unit to photograph the substrate before the substrate is printed on and to photograph the substrate after the substrate is printed on, and a control part to compare a first image of the substrate before the substrate is printed on with a second image of the substrate after the substrate is printed on through the camera unit and to determine whether the printing operation is accurately performed on the substrate.

The apparatus may further comprise a moving part to movably support the camera unit and the print head such that the camera unit and the print head are integrally moved.

The camera unit may comprise a first camera to photograph the substrate before the substrate is printed on and a second camera to photograph the substrate after the substrate is printed on.

The first camera may be disposed adjacent to the print head in a leading position with respect to a moving direction of the print head. The second camera may be disposed adjacent to the print head opposite the first camera in a trailing position with respect to the moving direction of the print head.

The camera unit may comprise a camera being disposed in either the leading position or the trailing position with respect to the moving direction of the print head in order to photograph the substrate before the substrate is printed on and to photograph the substrate after the substrate is printed on.

The control part may include a reference pattern to be printed on the substrate by the print head, and the control part compares a remaining image after subtracting the first image from the second image with the reference pattern to determine whether the printing operation is accurately performed on the substrate.

The apparatus may further comprise a display part to display whether the printing operation is performed on the substrate accurately or inaccurately as determined by the control part and to display the remaining image after subtracting the first image from the second image.

The camera unit may photograph the substrate before the substrate is printed on and after the substrate is printed on simultaneous with the printing operation performed by the print head.

The foregoing and/or other aspects of the present general inventive concept are also achieved by providing a method of controlling a substrate inspecting apparatus to inspect a substrate being printed on by a print head to determine whether a printing operation is accurately performed, the method comprising photographing the substrate before the substrate is printed on, photographing the substrate after the substrate is printed on, and comparing a first image of the substrate before the substrate is printed on with a second image of the substrate after the substrate is printed on and determining whether the printing operation is accurately performed on the substrate.

Photographing the substrate before the substrate is printed may comprise using a first camera disposed in a leading position with respect to a moving direction of the print head to photograph the substrate before the substrate is printed on. Additionally, photographing the substrate after the substrate is printed on may comprise using a second camera disposed in a trailing position with respect to the moving direction of the print head to photograph the substrate after the substrate is printed on. The method may further comprise moving the first camera, the print head, and the second camera integrally.

Photographing the substrate may comprise using a single camera disposed in either the leading position or the trailing position with respect to the moving direction of the print head to photograph the substrate before the substrate is printed on and to photograph the substrate after the substrate is printed on. The method may further comprise moving the print head and the camera integrally.

The method may further comprise providing a reference pattern to be printed on the substrate by the print head and comparing a remaining image after subtracting the first image from the second image with the reference pattern to determine whether the printing operation is being accurately performed on the substrate.

BRIEF DESCRIPTION OF THE DRAWINGS

These and/or other aspects and advantages of the present general inventive concept will become apparent and more readily appreciated from the following description of the embodiments, taken in conjunction with the accompanying drawings of which.

DETAILED DESCRIPTION OF THE PREFERRED EMBODIMENTS

Figure 1:
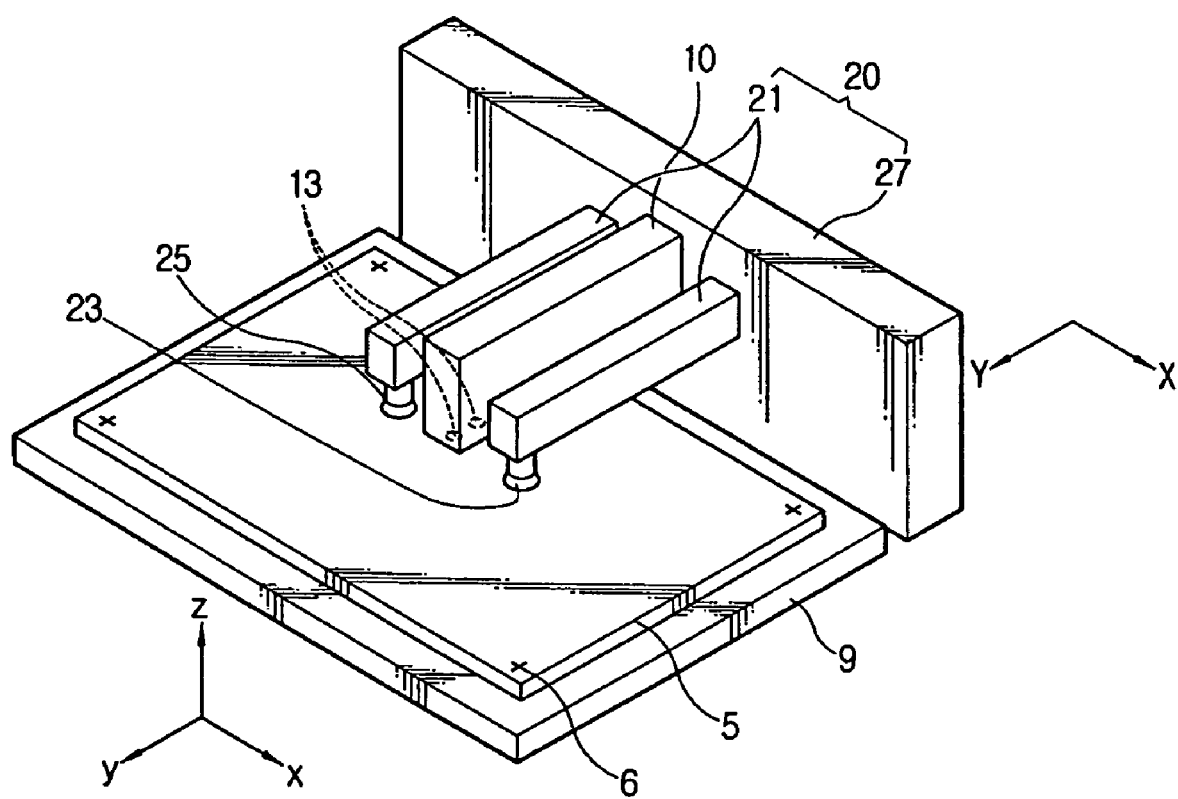
FIG. 1 is a perspective view illustrating a printing process with a substrate inspecting apparatus according to an embodiment of the present general inventive concept.

Reference will now be made in detail to the embodiments of the present general inventive concept, examples of which are illustrated in the accompanying drawings, wherein like reference numerals refer to the like elements throughout. The embodiments are described below in order to explain the present general inventive concept by referring to the figures.

FIG. 1 is a perspective view illustrating a printing process with a substrate inspecting apparatus according to an embodiment of the present general inventive concept.

The printing process refers to a process of forming a color filter on a substrate 5, employing an inkjet device. The inkjet device may be used with the substrate 5, a stage 9 provided on a lower side of the substrate 5 to movably support the substrate 5, a print head 10 to perform a printing operation on the substrate 5, and a moving part 27 to movably support the print head 10. The substrate inspecting apparatus 20 inspects the substrate 5 being printed on by the print head 10 during the printing process.

The substrate 5 is formed with a plate-shaped glass used in manufacturing display panels for flat display apparatuses, such as a TFT-LCD or an organic ELD. The substrate 5 includes a plurality of pixels (not shown) formed thereon at regular intervals. Each of the plurality of pixels (not shown) is printed on with ink ejected from one of a plurality of orifices 13 of the print head 10 to be described later. The substrate 5 also includes a plurality of alignment marks 6 formed thereon to be used as reference points to align a moving direction of the print head 10 with an aligning direction of the plurality of pixels (not shown) formed on the substrate 5. The substrate 5 may be transparent, semi-transparent, or opaque. Further, the substrate 5 may be used to form the display panel, but may also be used in other applications in which substrates are printed on by an ink jet device including, for example, semiconductors.

The stage 9 is also plate-shaped and is provided on the lower side of the substrate 5 so that it supports the substrate 5. Further, the stage 9 can movably support the substrate 5 in order to allow the substrate 5 to be aligned with the print head 10. The stage 9 may movably support the substrate 5 in a planar direction of the substrate 5 so that the alignment marks 6 of the substrate 5 are aligned with the moving direction of the print head 10. In other words, the stage 9 may be movable in two axial directions (x, y) perpendicular to each other in the planar direction of the substrate 5. The stage 9 may also be rotatable about another axial direction (z) transverse to the planar direction of the substrate 5 and perpendicular to the two axial directions (x, y). Further, the two axial motion directions (x, y) of the stage 9 may be set differently from or the same as the moving direction of the print head including two axial directions (X, Y) to be described later.

The print head 10 comprises the plurality of orifices 13 from which ink is ejected onto the plurality of pixels (not shown) of the substrate 5. The plurality of orifices 13 eject ink to form the color filter having colors including R (red), G (green), and B (blue), for example, if the display panel is produced for a TFT-LCD. The print head 10 is supported by the moving part 27 and is movable in the two axial directions (X, Y).

Figure 2:
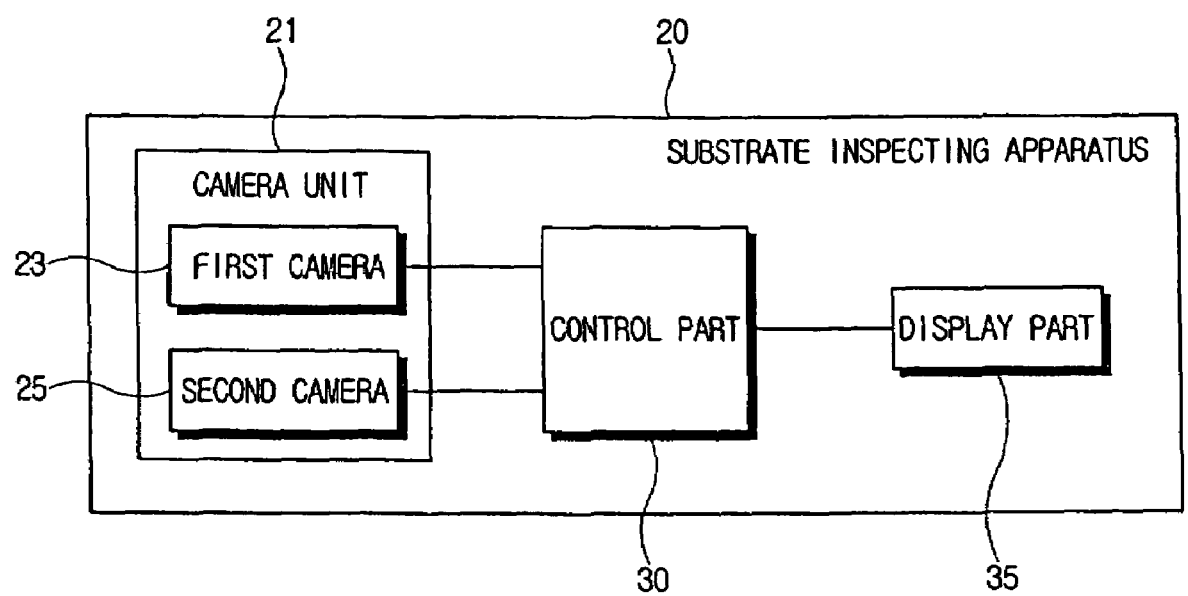
FIG. 2 is a control block diagram of the substrate inspecting apparatus of FIG. 1.

As illustrated in FIGS. 1 and 2, the substrate inspecting apparatus 20 according to the present general inventive concept comprises a camera unit 21 to photograph the substrate 5 before the substrate is printed on and to photograph the substrate 5 after the substrate is printed on while the printing operation is being performed by the print head 10, and a control part 30 to receive and compare a first image A of the substrate 5 photographed by the camera unit 21 before the substrate is printed on and a second image B of the substrate 5 photographed after the substrate is printed on and to determine whether the printing operation is accurately being performed on the substrate 5. The substrate inspecting apparatus 20 further comprises a moving part 27 to movably support the camera unit 21. The substrate inspecting apparatus 20 may further comprise a display part 35 to display whether the printing operation is being performed on the substrate 5 accurately or inaccurately, as determined by the control part 30.

The moving part 27 movably supports the camera unit 21 and the print head 10. The moving part 27 may have a composite structure or may be two separately movable components to movably support the camera unit 21 and the print head 10, respectively. The moving part 27 may movably support the camera unit 21 and the print head 10 in the two axial directions (X, Y). The moving part 27 may have a moving distance error within approximately 10 micrometers (μm) and may use a linear motion (LM) guide and/or a ball screw. Accordingly, the moving part 27 moves the camera unit 21 and the print head 10 along the aligning direction of the plurality of pixels (not shown) formed on the substrate 5.

Namely as illustrated in FIG. 1, during the printing and/or inspection operation(s), the camera unit 21 and the print head 10 are first moved by the moving part 27 in the X direction to photograph and print on an array of pixels extending along the X direction of the substrate 5. Then, the camera unit 21 and the print head 10 are moved in the Y direction by the moving part 27 to align the camera unit 21 and the print head 10 with a another array of pixels also extending along the X direction of the substrate 5. The camera unit 21 and the print head 10 are again moved in the X direction to photograph and print on the other array of pixels on the substrate 5. Movement above the array of pixels along the X direction may be converse to movement above the other array of pixels along the X direction.

The camera unit 21 comprises a first camera 23 to photograph the substrate 5 before the substrate is printed on and a second camera 25 to photograph the substrate 5 after the substrate is printed on. The camera unit 21 may be supported by the moving part 27, thereby allowing the camera unit 21 to be moved integrally with the print head 10. Alternatively, the camera unit 21 may be moved by the moving part 27 separately from the print head 10.

When the print head 10 is moved in the X direction toward a right side in FIG. 1, the first camera 23 is disposed in a leading position in the moving direction of the print head 10 to photograph the substrate 5 before the substrate is printed on. That is, when the print head 10 is moved in the X direction toward the right side in FIG. 1, the first camera 23 is positioned on the right side of the print head 10. However, when the print head 10 is moved in the X direction toward a left side in FIG. 1, the first camera 23 is disposed in a trailing position in the moving direction of the print head 10 to photograph the substrate 5 after the substrate is printed on.

Similarly, when the print head 10 is moved in the X direction toward the right side in FIG. 1, the second camera 25 is disposed in the trailing position in the moving direction of the print head 10 to photograph the substrate 5 after the substrate is printed on. That is, when the print head 10 is moved in the X direction toward the right side in FIG. 1, the second camera 25 is disposed on the left side of the print head 10. However, when the print head 10 is moved in the X direction toward the left side in FIG. 1, the second camera 25 is disposed in the leading position in the moving direction of the print head 10 to photograph the substrate 5 before the substrate is printed on.

The control part 30 includes a reference pattern C to be printed on the substrate 5 by the print head 10. The control part 30 compares a remaining image after subtracting a first image A (created by the camera in the leading position) from the second image B (created by the camera in the trailing position) with the reference pattern C and determines whether the printing operation is being performed accurately on the substrate 5. As illustrated in FIG. 2, the control part 30 receives the first image A and the second image B from the first camera 23 and the second camera 25, respectively, and compares the remaining image after subtracting the first image A from the second image B with the reference pattern C. The control part 30 determines that the printing operation is being performed accurately on the substrate 5 when the remaining image corresponds with the reference pattern C and displays a corresponding result of the determination on the display part 35. The control part 30 determines that the printing operation is being performed inaccurately on the substrate 5 when the remaining image does not correspond with the reference pattern C and displays the corresponding result of the determination on the display part 35.

The display part 35 may display the corresponding result of the determination made by the control part 30 of whether the printing operation is being performed accurately on the substrate 5 by the print head 10. The display part 35 may also display the first image A photographed by the first camera 23, the second image B photographed by the second camera 25, and the remaining image after subtracting the first image A from the second image B. Accordingly, a user may use the display part 35 to ascertain an accuracy of the printing operation being performed on the substrate 5.

Figure 3:
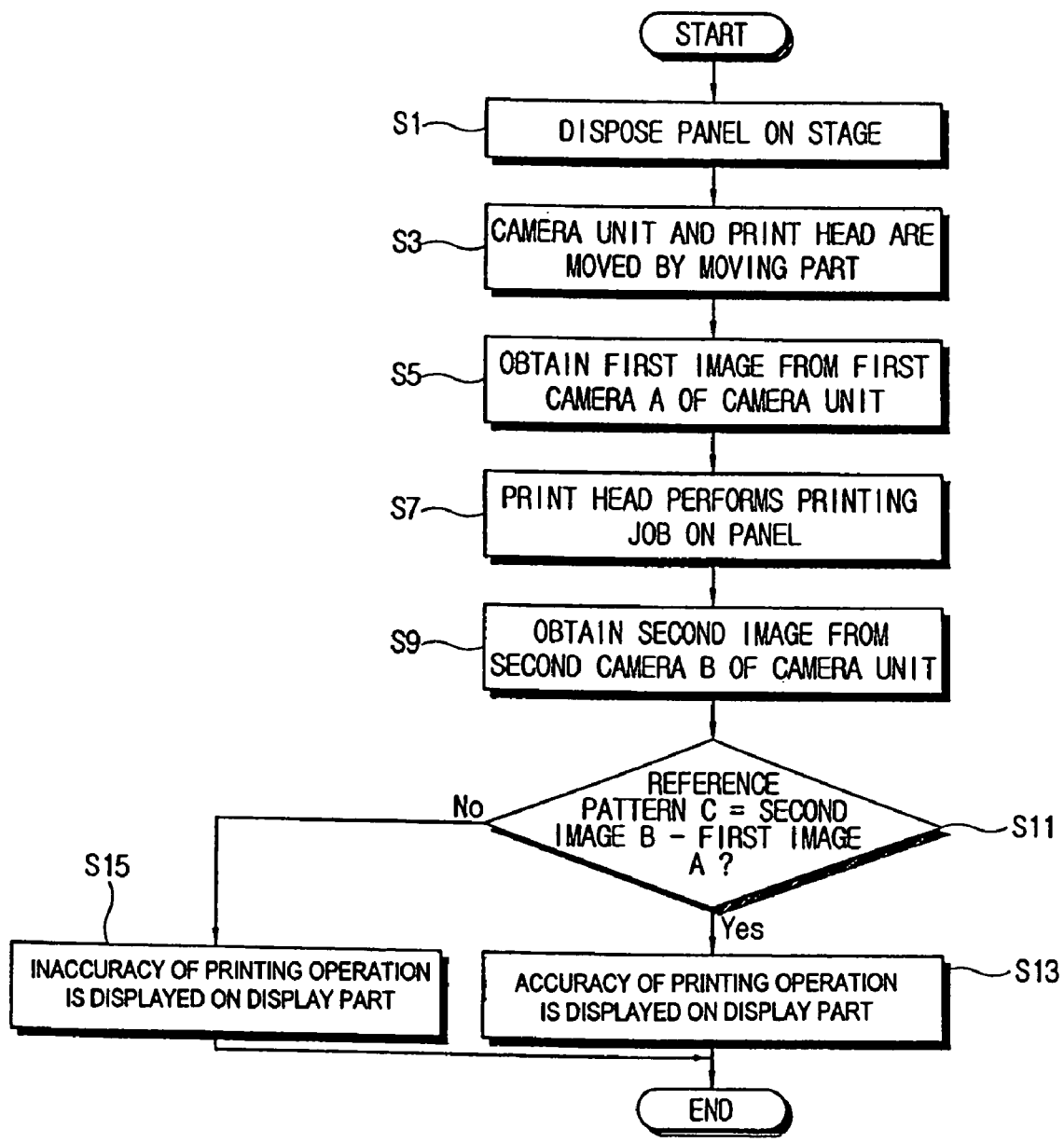
FIG. 3 is a flow chart illustrating a method of controlling the substrate inspecting apparatus according to another embodiment of the present general inventive concept.

A method of controlling the substrate inspecting apparatus 20 of FIG. 1 according another embodiment of the present general inventive concept will now be described with reference to FIG. 3. The substrate 5 is first disposed on the stage 9 (operation S1). At this time, it may be ascertained whether the substrate 5 is properly positioned on the stage 9. That is, the stage 9 is controlled so that the alignment marks 6 of the substrate 5 correspond to the moving direction of the print head 10 while the print head 10 is performing the printing operation. The camera unit 21 and the print head 10 are moved by the moving part 27 (operation S3), and the first image A of the substrate 5 before the substrate is printed on is obtained by the first camera 23 of the camera unit 21 (operation S5). A printing operation is performed on the substrate 5 by the print head 10 (operation S7), and the second image B of the substrate 5 after the substrate is printed on is obtained by the second camera 25 of the camera unit 21 (operation S9). The operation of obtaining the first and second images A and B and performing the printing operation may be performed simultaneously, in real time. Thereafter, the first image A and the second image B are transmitted to the control part 30, and the control part 30 compares the remaining image after subtracting the first image A from the second image B with the reference pattern C to determine whether the printing operation is performed accurately on the substrate 5 (operation S11). When the remaining image after subtracting the first image A from the second image B corresponds with the reference pattern C, accuracy of the printing operation of the substrate 5 is displayed on the display part 35 (operation S13). If not, inaccuracy of the printing operation of the substrate 5 is displayed on the display part 35 (operation S15).

Accordingly, the substrate inspecting apparatus 20 according to the previous embodiment of the present general inventive concept photographs the first image A of the substrate 5 before the substrate is printed on and the second image B of the substrate 5 after the substrate is printed on through the camera unit 21, and can precisely inspect the substrate 5 being printed on by the print head 10, since the first image A and the second image B are compared and the accuracy of the printing operation performed on the substrate 5 is determined.

The camera unit 21 and the print head 10 can be provided to be integrally moved. Thus, the printing operation performed on the substrate 5 and the photographing operation to inspect the substrate 5 can be conducted simultaneously, thereby reducing inspection time. Also, the substrate inspecting apparatus 20 can be used with opaque substrates as well as transparent substrates.

Figure 4:
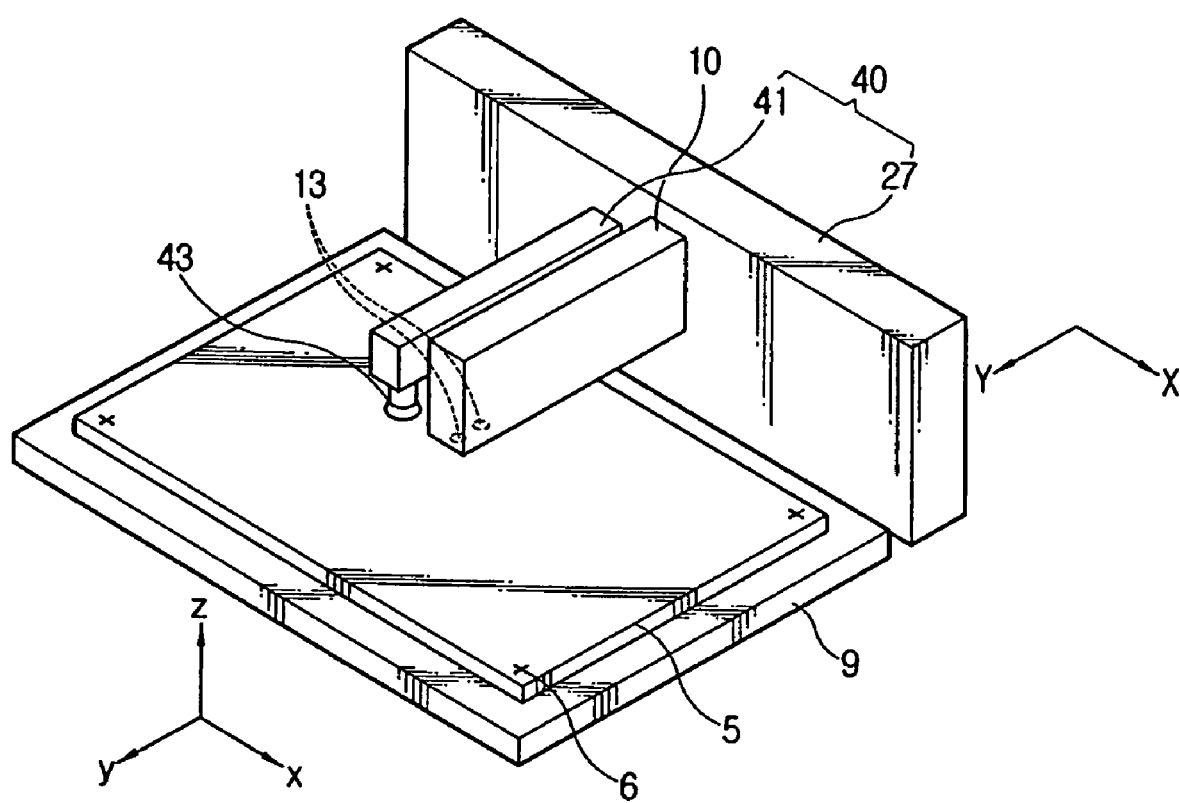
FIG. 4 is a perspective view illustrating a printing process with a substrate inspecting apparatus according to another embodiment of the present general inventive concept.

FIG. 4 is a perspective view illustrating a printing process with a substrate inspecting apparatus according to another embodiment of the present general inventive concept. A camera unit 41 of the substrate inspecting apparatus 40 according to the present embodiment comprises a camera 43 disposed in either a leading position or a trailing position in the moving direction of the print head 10 to photograph the substrate 5 before the substrate is printed on and to photograph the substrate 5 after the substrate is printed on.

The camera 43 is provided in the trailing position in the moving direction of the print head 10. The camera 43 is supported by the moving part 27 so that the camera 43 can be moved integrally with the print head 10. The camera 43 may be provided in the leading position in the moving direction of the print head 10. The camera 43 may first photograph the entire substrate 5 before the print head 10 performs the printing operation to obtain a first image A (i.e., scans the substrate 5). The camera 43 may then be positioned in the trailing position to photograph the substrate 5 after it is printed on while the print head 10 performs the printing operation on the substrate 5 to obtain the second image B. Thereafter, accuracy of the printing operation performed on the substrate 5 is determined by the control part 30 as described above.

With reference to FIG. 4, a method of controlling the substrate inspecting apparatus 40 according to another embodiment of the general inventive concept will be described. The substrate 5 is first disposed on the stage 9. The camera unit 41 and the print head 10 are moved by the moving part 27 in order to photograph and print on the substrate 5. That is, the first image A of the substrate 5 before printing thereon is obtained through the camera 43 of the camera unit 41 before the printing operation by scanning the entire substrate 5. The print head 10 then performs the printing operation on the substrate 5 while the camera 43 simultaneously obtains the second image B of the substrate 5 after the substrate is printed on. Thereafter, the first image A and the second image B are transmitted to the control part 30 so that the control part 30 can compare the remaining image after subtracting the first image A from the second image B with the reference pattern C to determine whether the printing operation is performed on the substrate 5 accurately or inaccurately. The result of the determination is displayed on the display part 35.

The substrate inspecting apparatus 40 according to the embodiment of FIG. 4 is provided with a single camera 43 on the camera unit 41, thereby having a simplified structure and reducing a production cost in comparison with the embodiment of FIG. 1. In addition, the first image A before the substrate 5 is printed on and the second image B after the substrate is printed on are photographed through the camera unit 41, they are compared to determine the accuracy of the printing operation performed on the substrate 5, thereby precisely inspecting the printing operation performed by the print head 10 on the substrate 5.

The camera unit 41 and the print head 10 are provided to be integrally movable, and thus, the printing operation performed on the substrate 5 and the photographing operation to inspect the substrate 5 are conducted simultaneously, thereby reducing the inspection time. Also, the substrate inspecting apparatus 40 can be used with opaque substrates as well as transparent substrates.

As described above, the printing operation performed on the substrate can be precisely inspected according to the present general inventive concept. Further, printing on the substrate and photographing the substrate to perform an inspection are conducted simultaneously, thereby reducing the inspection time. The substrate inspecting apparatus can be used with opaque substrates.

Although the present general inventive concept has been described in connection with the exemplary embodiments illustrated in the accompanying drawings, it should be understood that the present general inventive concept is not limited thereto and those skilled in the art can make various modifications and changes without departing from the scope of the general inventive concept.

What is claimed is:

1. A substrate inspecting apparatus to inspect a substrate printed on by a print head to determine if a printing operation is accurately performed, comprising:
   a camera unit to photograph the substrate before the substrate is printed on and to photograph the substrate after the substrate is printed on; and
   a control part to subtract a first image of the substrate before the substrate is printed on from a second image of the substrate after the substrate is printed on through the camera unit to yield a remaining image, and to compare the remaining image with a reference pattern to determine whether the printing operation is accurately performed on the substrate.

2. The apparatus as claimed in claim 1, further comprising:
   a moving part to movably support the camera unit and the print head so that the camera unit and the print head are integrally moved.

3. The apparatus as claimed in claim 2, wherein the camera unit comprises a first camera to photograph the substrate before the substrate is printed on and a second camera to photograph the substrate after the substrate is printed on.

4. The apparatus as claimed in claim 3, wherein the first camera is disposed in a leading position in a moving direction of the print head and the second camera is disposed in a trailing position in the moving direction of the print head.

5. The apparatus as claimed in claim 2, wherein the camera unit comprises a camera being disposed in one of a leading position and a trailing position in a moving direction of the print head to photograph the substrate before the substrate is printed on and to photograph the substrate after the substrate is printed on.

6. The apparatus as claimed in claim 1, wherein the control part includes the reference pattern to be printed on the substrate by the print head.

7. The apparatus as claimed in claim 6, further comprising:
   a display part to display whether the printing operation is performed on the substrate accurately or inaccurately as determined by the control part and to display the remaining image after subtracting the first image from the second image.

8. The apparatus as claimed in claim 1, wherein the camera unit photographs the substrate before the substrate is printed on and after the substrate is printed on simultaneous with the printing operation performed by the print head.

9. An apparatus to inspect a substrate having a printing operation being performed thereon by a print head such that one or more orifices on the print head eject one or more ink droplets to one or more pixels on the substrate, the apparatus comprising:
   a substrate supporting part;
   a print head disposed above the substrate supporting part to perform the printing operation on the substrate;
   a camera unit to photograph the substrate during the printing operation to obtain a first image of at least one pixel of the substrate before having ink ejected thereon, and to obtain a second image of the at least one pixel of the substrate after ink is ejected thereon; and a control part to subtract the first image from the second image to create a remaining image and to compare the remaining image with a predetermined reference pattern.

10. The apparatus as claimed in claim 9, wherein the control part is able to determine whether the ink is properly positioned on the at least one pixel of the substrate.

11. The apparatus as claimed in claim 10, wherein if the remaining image matches the predetermined reference pattern, the control part determines that the ink is properly positioned on the at least one pixel of the substrate, and if the remaining image does not match the predetermined reference pattern, the control part determines that the ink is not properly positioned on the at least one pixel of the substrate.

12. The apparatus as claimed in claim 9, further comprising:

a display part to indicate whether the print head is performing the printing operation accurately on the substrate.

13. The apparatus as claimed in claim 12, wherein the display part further displays a comparison between a difference of the first image and the second image and a predetermined reference pattern.

14. The apparatus as claimed in claim 9, wherein the substrate supporting part is a stage that movably supports the substrate and the substrate includes one or more alignment marks to perform an initial alignment between the substrate and a moving direction of the print head.

15. The apparatus as claimed in claim 9, further comprising:

a moving part to integrally move the camera unit and the print head in a print head moving direction along the substrate.

16. The apparatus as claimed in claim 15, wherein the camera unit comprises a camera disposed in a trailing position with respect to the print head in the moving direction.

17. The apparatus as claimed in claim 16, wherein the camera unit scans the substrate including the at least one pixel to obtain the first image before the print head begins the printing operation.

18. The apparatus as claimed in claim 16, wherein during the printing operation, the print head ejects ink to a current pixel, and when the print head and the camera unit are moved in the moving direction to position the print head to correspond with a next pixel the camera unit photographs the current pixel.

19. The apparatus as claimed in claim 15, wherein the camera unit comprises a first camera disposed in a leading position with respect to the print head in the moving direction and a second camera disposed in a trailing position with respect to the print head in the moving direction.

20. The apparatus as claimed in claim 19, wherein during the printing operation, the first camera photographs a next pixel, the print head ejects ink to a current pixel, and the second camera photographs a previous pixel; and when the first camera, the print head, and the second camera are moved in the moving direction the print head ejects ink to the next pixel and the second camera photographs the current pixel.

21. The apparatus as claimed in claim 9, wherein the substrate is one of an opaque substrate and a transparent substrate.

22. A method of controlling a substrate inspecting apparatus to inspect a substrate being printed on by a print head to determine if a printing operation is accurately performed, the method comprising:

photographing the substrate before the substrate is printed on;

photographing the substrate after the substrate is printed on; and subtracting a first image of the substrate before the substrate is printed on from a second image of the substrate after the substrate is printed on to yield a remaining image; and comparing the remaining image with a reference pattern to determine whether the printing operation is accurately performed on the substrate.

23. The method as claimed in claim 22, wherein the photographing of the substrate before the substrate is printed on comprises using a first camera disposed in a leading position in a moving direction of the print head to photograph the substrate before the substrate is printed on.

24. The method as claimed in claim 23, wherein the photographing of the substrate after the substrate is printed on comprises using a second camera disposed in a trailing position in the moving direction of the print head to photograph the substrate after the substrate is printed on.

25. The method as claimed in claim 24, further comprising:

moving the first camera, the print head, and the second camera integrally in the moving direction of the print head along the substrate.

26. The method as claimed in claim 22, wherein the photographing of the substrate comprises using a single camera disposed in one of a leading position and a trailing position in a moving direction of the print head to photograph the substrate before the substrate is printed on and to photograph the substrate after the substrate is printed on.

27. The method as claimed in claim 26, further comprising:

moving the print head and the camera integrally in the moving direction of the print head along the substrate.

28. The method as claimed in claim 22, further comprising:

providing a reference pattern to be printed on the substrate by the print head.

29. The method as claimed in claim 22, wherein the photographing of the substrate before the substrate is printed on and after the substrate is printed on is performed simultaneously with the printing operation performed by the print head.

30. A method of controlling an apparatus to inspect a substrate having a printing operation being performed thereon by a print head such that one or more orifices on the print head eject one or more ink droplets to one or more pixels on the substrate, the method comprising:

performing the printing operation on the substrate using a print head disposed above the substrate;

photographing the substrate during the printing operation to obtain a first image of at least one pixel of the substrate before having ink ejected thereon, and to obtain a second image of the at least one pixel of the substrate after ink is ejected thereon using a camera unit;

subtracting the first image from the second image to yield a remaining image; and comparing the remaining image with a predetermined reference pattern.

31. The method as claimed in claim 30, wherein the comparing operation is able to determine whether the ink is properly positioned on the at least one pixel of the substrate using a control part.

32. The method as claimed in claim 31, wherein if the remaining image matches the predetermined reference pattern, determining that the ink is properly positioned on the at least one pixel of the substrate, and if the remaining image does not match the predetermined reference pattern, determining that the ink is not properly positioned on the at least one pixel of the substrate.

33. The method as claimed in claim 30, further comprising:
displaying whether the print head is performing the printing operation accurately on the substrate using a display part.

34. The method as claimed in claim 33, further comprising:
displaying a comparison between the remaining image and the predetermined reference pattern using the display part.

35. The method as claimed in claim 30, further comprising:
before performing the printing operation, performing an initial alignment of the substrate with a moving direction of the print head using one or more alignment marks on the substrate.

36. The method as claimed in claim 30, further comprising:
integrally moving the camera unit and the print head in a print head moving direction along the substrate using a moving part.

37. The method as claimed in claim 36, wherein the photographing of the substrate during the printing operation comprises using a camera disposed in a trailing position with respect to the print head in the moving direction to obtain the second image of the at least one pixel of the substrate after ink is ejected thereon.

38. The method as claimed in claim 37, wherein the obtaining of the first image comprises scanning the substrate including the at least one pixel to obtain the first image before the print head begins the printing operation.

39. The method as claimed in claim 37, wherein during the printing operation, the print head ejects ink to a current pixel, and the camera unit photographs the current pixel when the print head and the camera unit are moved in the moving direction so that the print head corresponds to a next pixel.

40. The method as claimed in claim 36, wherein the photographing of the substrate during the printing operation comprises using a first camera disposed in a leading position with respect to the print head in the moving direction and a second camera disposed in a trailing position with respect to the print head in the moving direction to obtain the first image and the second image, respectively.

41. The method as claimed in claim 40, wherein during the printing operation, the first camera photographs a next pixel, the print head ejects ink to a current pixel, and the second camera photographs a previous pixel; and when the first camera, the print head, and the second camera are moved in the moving direction the print head ejects ink to the next pixel and the second camera photographs the current pixel.

42. The method as claimed in claim 30, wherein the substrate is one of an opaque substrate and a transparent substrate.

\* \* \* \* \*